(12) United States Patent
Hornung et al.

(10) Patent No.: US 8,100,173 B2
(45) Date of Patent: Jan. 24, 2012

(54) METHOD OF PRODUCING INCONTINENCE ARTICLES IN THE FORM OF PANTS

(75) Inventors: Fridmann Hornung, Penalolén Santiago (CL); Benjamin Wenzel, Heidenheim (DE); Wolfgang Ostertag, Gerstetten (DE)

(73) Assignee: Paul Hartmann Aktiengesellschaft, Heidenheim (DE)

( * ) Notice: Subject to any disclaimer, the term of this patent is extended or adjusted under 35 U.S.C. 154(b) by 182 days.

(21) Appl. No.: 12/314,712

(22) Filed: Dec. 16, 2008

(65) Prior Publication Data

US 2009/0178755 A1 Jul. 16, 2009

(30) Foreign Application Priority Data

Dec. 20, 2007 (DE) .......................... 10 2007 063 209

(51) Int. Cl.
 *B29C 65/00* (2006.01)
 *B32B 37/02* (2006.01)
 *B32B 38/04* (2006.01)
(52) U.S. Cl. ........ 165/265; 156/163; 156/178; 156/204; 156/211; 156/221; 156/226; 156/227; 156/229; 156/251; 156/265; 156/270
(58) Field of Classification Search .................. 156/229, 156/163, 204, 211, 221, 226, 227, 251, 265, 156/270, 178
See application file for complete search history.

(56) References Cited

U.S. PATENT DOCUMENTS

| | | | | |
|---|---|---|---|---|
| 4,936,839 A | * | 6/1990 | Molee et al. | .................. 604/378 |
| 5,643,396 A | | 7/1997 | Rajala | |
| 2002/0151864 A1 | | 10/2002 | Otsubo | |
| 2006/0254708 A1 | | 11/2006 | Wada | |
| 2009/0165941 A1 | * | 7/2009 | Wada | .............................. 156/250 |
| 2009/0326503 A1 | * | 12/2009 | Lakso et al. | ............. 604/385.23 |

FOREIGN PATENT DOCUMENTS

| | | |
|---|---|---|
| DE | 10 2005 011 059 | 8/2006 |
| DE | 10 2005 032 221 | 1/2007 |
| DE | 10 2005 048 868 | 4/2007 |
| EP | 1 504 738 | 2/2005 |
| EP | 1 574 191 | 9/2005 |
| EP | 1 661 535 | 5/2006 |
| EP | 1 736 126 | 12/2006 |
| EP | 1 806 117 | 7/2007 |
| EP | 1 813 234 | 8/2007 |
| EP | 1 842 516 | 10/2007 |
| EP | 1 867 311 | 12/2007 |
| JP | 01136103 * | 2/1999 |
| JP | 2003 126148 | 5/2003 |
| WO | 2004/052260 | 6/2004 |
| WO | 2007/067103 | 6/2007 |

* cited by examiner

*Primary Examiner* — Linda L Gray
(74) *Attorney, Agent, or Firm* — Paul Vincent

(57) ABSTRACT

A continuous method for producing incontinence articles in the form of pants for receiving body excrements utilizes crotch sections comprising absorbent bodies and having leg cut-outs formed by a first contour cut. Two partial webs are joined to the crotch sections in such a fashion that one end of the crotch sections overlaps one partial web in a longitudinal direction transversely to the machine direction, and the other end thereof overlaps the other partial web, and the crotch sections are disposed at a separation from each other in the machine direction. A second contour cut is performed that includes the partial webs on their mutually facing edge sections for forming substantially curved leg cut-outs. The article is then folded and the partial webs are joined transversely to the machine direction at a separation from each other for forming side seam areas of the incontinence article to be produced.

19 Claims, 9 Drawing Sheets

METHOD OF PRODUCING INCONTINENCE ARTICLES IN THE FORM OF PANTS

BACKGROUND OF THE INVENTION

The invention concerns a continuous method for producing incontinence articles in the form of pants for receiving body excrements, comprising a front belly section and a rear back section, which are connected to each other at side seam areas on both sides during production to form a belly and back band, which is continuous in the transverse or peripheral hip direction and has a hip opening that is closed in the peripheral hip direction, and a crotch section which has an absorbent body and extends in a longitudinal direction between the belly section and the back section, and is permanently attached to the belly section and to the back section, wherein the crotch section as well as the belly section and the back section define the leg openings of the incontinence article, wherein first elastification means are provided in the belly section and the back section, which extend in the transverse or peripheral hip direction at a separation from each other and parallel to each other to extensively elastify the belly area and the back area, wherein second elastification means are provided in an area of the belly section and the back section on the crotch side facing the leg openings (i.e. remote from the hip), which extend starting from the two side seam areas towards a longitudinal center axis of the incontinence article in a curved shape, thereby fanning out with increasing separation from each other.

A three-component incontinence article of this type is disclosed e.g. in the German patent application DE 10 2007 055524.7 of the Assignee, which has not been previously published.

In this specific product concept, an H-shaped basic structure of the incontinence article is realized by joining the crotch section, which extends in the longitudinal direction, to the belly section, which extends substantially in the transverse or peripheral hip direction, and to the correspondingly extending back section when these three components are flatly extended. The incontinence article is then modularly designed from the components crotch section, belly section and back section. These components are advantageously initially connected to each other via the crotch section, and preferably after that, the side seam areas of the belly section are connected to those of the back section on both sides. This connection is realized by the manufacturer to obtain the shape of pants. This connection is typically permanent. However, it may also be provided that the pants can be opened, in particular, along a breaking line which may extend, in particular, in the side seam area, e.g. for removing a used incontinence article from a person who is in need of care.

Incontinence articles in the form of pants differ, in principle, from incontinence articles of normal diaper shape that can be opened and closed in that the hip size is generally predetermined and the article can be adjusted to different body sizes by providing a number of different basic sizes that can be elastically stretched. Towards this end, elastification means, in particular, in the form of bands or threads, often called LYCRA® (elastane) threads, are generally connected in a prestrained state (stretch-bond method) to chassis materials of the incontinence article, i.e. they are fixed in the prestrained state to the chassis materials e.g. by means of glue. Due to their pretension, these elastification means gather the chassis materials to thereby form crimps. The incontinence article or the elasticised chassis materials of the incontinence article can be elastically stretched again when the incontinence article is applied, like pants, to the user.

Several incontinence articles in the form of pants comprising elasticised chassis materials of this type have been disclosed and are also discussed e.g. in the above-mentioned document WO 2004/052260 A1.

It is difficult to produce an optimum contour of the leg openings, in particular, when working at high machine speed, in particular in a range of several 100 m/min, which is normal during production of modern incontinence articles, since both the crotch section and the belly and back section of the incontinence article define the leg openings.

It is the underlying purpose of the present invention to provide a continuous method for producing an incontinence article in the form of pants having the above-mentioned features, which takes into account, in particular, the above-mentioned aspects of providing the leg opening contour and which can be economically performed.

SUMMARY OF THE INVENTION

In accordance with the invention, this object is achieved by a method comprising the following method steps:
  supplying crotch sections which comprise absorbent bodies and leg cut-outs formed by a first contour cut;
  supplying two partial webs based on non-woven material, which form the subsequent belly section and the subsequent back section of the incontinence article;
  supplying and applying the second elastification means to both partial webs and fixing them thereto;
  joining the crotch sections with the two partial webs in such a fashion that one end of the crotch sections overlaps one partial web in a longitudinal direction transversely to the machine direction, and the other end thereof overlaps the other partial web, and that the crotch sections are disposed at a separation from each other in the machine direction, fixing the crotch sections and partial webs in the overlapping areas, and forwarding in the machine direction;
  supplying, applying and fixing the first elastification means to the partial webs in the machine direction;
  performing a second contour cut that includes the partial webs on their mutually facing edge sections for forming substantially curved leg cut-outs;
  folding about a folding line that extends in the machine direction in such a fashion that one partial web comes to rest on top of the other partial web;
  joining the partial webs, which are disposed on top of each other, transversely to the machine direction at a separation from each other for forming side seam areas of the incontinence article to be produced, and obtaining products that comprise a belly section, a back section and an intermediate crotch section;
  performing a separating cut in a direction transversely to the machine direction and obtaining separated finished incontinence articles.

Since the leg cut-outs are realized in two steps, i.e. by a first contour cut, which is performed on the crotch section of the hygiene article, and a second contour cut, which is performed on both partial webs which form the belly section or the back section of the incontinence article, shaping can be optimized. In this fashion, the respective single contour cut is also shorter.

Moreover, one single cut can be better adjusted to the machine direction. The cutting devices for the contour cut can also be optimized with respect to the materials to be cut, e.g. different cutting knifes can be used for different materials.

In accordance with a preferred embodiment of the inventive method, a non-woven material cover layer that extends over the second elastification means is supplied to and disposed on each partial web after supplying, applying, and fixing the second elastification means to the partial webs, and the two partial webs are further supplied in the machine direction at a separation from each other and parallel to each other.

In accordance with another preferred embodiment of the inventive method, a non-woven material cover layer that extends over the first elastification means is applied to each partial web after supplying, applying and fixing the first elastification means in the machine direction to the partial webs, and the two partial webs are further supplied in the machine direction at a separation from and parallel to each other.

It is basically feasible to previously configure the crotch sections of the incontinence article, which are to be supplied, in such a fashion that they are supplied in an endless fashion, in particular, from a roll, and already have the first contour cut for forming the leg cut-outs on the crotch section. In accordance with a further embodiment of the inventive method, it may be advantageous for the crotch sections to be supplied to have, in particular, a uniform width, and to perform the first contour cut for forming the leg cut-outs of the crotch section within the continuous method.

In accordance with a further method variant, it may be advantageous for the crotch sections to be formed within the continuous method and not before, by supplying an endless topsheet material web, an endless backsheet material web and absorbent bodies in a machine direction, disposing the absorbent bodies at a separation from each other between the topsheet material web and the backsheet material web, and securing the composite formed in this fashion. The first contour cut is then performed in the composite formed in this fashion, in order to form the leg cut-outs of the subsequent crotch sections of the incontinence article.

In another advantageous fashion, leg elastification means are supplied between the cover materials of the crotch section, i.e. between the topsheet material web and the backsheet material web. The leg elastification means are moreover advantageously supplied in such a fashion that they extend at a varying separation from the absorbent body and have, at their longitudinal ends, a larger separation from the absorbent body than in the center. The leg elastification means are preferentially supplied in a curved shape. In a particularly advantageous fashion, the leg elastification means are supplied in such a fashion that the leg elastification means substantially follow the curved leg cut-outs of the subsequent crotch section.

In a preferred embodiment of the method, the first contour cut is performed in such a fashion that it substantially forms curved leg sections of the subsequent crotch sections of the incontinence article.

In a particularly preferred embodiment, the first contour cut is performed by means of a cutting roller pair, i.e. a rotating knife with an anvil roller.

The present invention is particularly advantageous exactly for the production of incontinence articles of this type, in which the crotch section has leg elastification means that are associated with the leg openings. If, in this case, the respective crotch sections are provided with leg elastification means and then separated, the leg elastification means exert strong tensile forces on the materials of the respective crotch section and try to pull the crotch section together. This is difficult to control by means of production technology, and it is even more difficult to provide the leg openings with a contour when the crotch sections are separated. In accordance with the present invention, that part of the leg openings, which is defined by the crotch section, is already produced during performance of the first contour cut, at a time at which the crotch sections are not yet separated, i.e. are still endlessly supplied. With this endless supply, the above explained forces, which are caused by the leg elastification means, can be better controlled, leading to a better result with respect to accuracy of contour of the leg openings with reduced technical effort.

It is basically feasible to supply the topsheet material web, backsheet material web and absorbent body components in the subsequent longitudinal direction of the crotch section or the hygiene article. Supply in the transverse direction is also feasible. In the first case, a 90° deflection is required in the course of the endless production method, since further production is preferably performed in the transverse direction of the incontinence article. In any event, the crotch sections must be separated, i.e. singled, in a direction transversely to the machine direction, and then be further supplied at a separation from each other in order to be connected to the endless partial webs.

The backsheet material web can be supplied in the form of a liquid-impermeable foil sheet, which is provided with a non-woven material coating prior to or during the continuous method, which can provide the outer side of the incontinence article facing away from the body with a textile impression. It may also be advantageous to provide a reinforcing coating of the backsheet material web in some areas. The reinforcing coating preferably consists of a non-woven material, in particular, a spunbonded non-woven material of polypropylene, in particular, having a surface density of 10 to 20 $g/m^2$, in particular of 12 to 17 $g/m^2$.

The backsheet material web comprises, in particular, a foil, in particular of a surface density of 18 to 40 $g/m^2$. The backsheet material web comprises, in particular, a foil, which is liquid-tight but at the same time breathable during use, i.e. a water vapor-permeable, in particular, microporous foil. The water vapor permeability of the backsheet material web, measured according to DIN 53 122-1 (Edition: 2001-08), is, in particular, at least 300 $g/m^2/24$ h, moreover, in particular at least 1000 $g/m^2/24$ h, moreover, in particular at least 2000 $g/m^2/24$ h, moreover, in particular at least 3000 $g/m^2/24$ h, moreover, in particular at least 4000 $g/m^2/24$ h, moreover, in particular at most 6000 $g/m^2/24$ h.

The absorbent body comprises materials that absorb body liquids, such as natural or synthetic fibers, in particular, cellulose fibers, preferably in the form of cellulose fluff. The absorbent body moreover preferably comprises super-absorbent materials (SAP), in particular, on the basis of surface-cross-linked, partially neutralized polyacrylates.

Thread-shaped or band-shaped elastification means, such as rubber or polyetherpolyurethane or polyesterpolyurethane threads, preferably elastic threads such as LYCRA® or SPANDEX® (elastane) threads are preferably used as leg elastification means. The leg elastification means preferably have a thickness of 300 to 1500 dtex, in particular 500 to 1200 dtex, moreover in particular 500 to 900 dtex.

The leg elastification means are advantageously fixed to the cover materials of the crotch section with a pretension of 1.5 to 6.0, in particular of 2.5 to 4.5.

The two partial webs that form the subsequent belly section and the subsequent back section may e.g. be supplied in that each partial web is unrolled from its own roll and supplied to the production process. In accordance with a preferred method variant, an endless non-woven material web may initially be supplied which is then separated along the machine direction to form the two partial webs. The machine thereby requires only one roll.

The partial webs on the basis of non-woven material for the subsequent belly section and/or the subsequent back section are preferably selected from the group of spunbonded non-woven materials, meltblown non-woven materials, SM non-woven materials, SMS non-woven materials, SMMS non-woven materials, card webs or Through Air bonded card webs. With particular preference, the partial webs for the subsequent belly section and/or the subsequent back section are produced from a spunbonded non-woven material. The non-woven materials that are used for the partial webs for the subsequent belly section and/or the subsequent back section advantageously have a surface density of 10 to 30 g/m$^2$, moreover preferably 15 to 25 g/m$^2$. A spunbonded non-woven material of polypropylene, in particular, with a surface density of 15 to 25 g/m$^2$, is preferentially used for the partial webs for the subsequent belly section and the subsequent back section.

The first and/or second elastification means are advantageously endlessly supplied to the partial webs in the machine direction. The first and the second elastification means are preferentially endlessly supplied to the partial webs in the machine direction.

The above-mentioned first elastification means that extend in the peripheral hip direction are advantageously introduced at a separation from each other of 4 to 10 mm, in particular 4 to 8 mm, in particular 4 to 6 mm.

The second elastification means that fan out in a curved shape in the direction towards the longitudinal center axis of the incontinence article are correspondingly introduced at a varying separation from each other (separation of directly neighboring elastification means) of between 3 mm and 35 mm. Guiding instruments that can be driven in an oscillating fashion are advantageously used for introducing the elastification means.

The second elastification means are advantageously introduced in such a fashion that a minimum separation between the second elastification means (i.e. the separation between directly neighboring second elastification means) in the subsequent side seam areas is 3 to 8 mm, in particular 3 to 7 mm, and moreover in particular 3 to 6 mm.

The second elastification means are moreover advantageously introduced in such a fashion that a maximum separation between the second elastification means (i.e. the separation between directly neighboring elastification means) on a subsequent absorbent body edge or on a subsequent longitudinal edge of the crotch section is 7 to 35 mm, in particular 10 to 32 mm, and moreover in particular 12 to 30 mm.

The separations between the second elastification means in the subsequent back section advantageously differ from the separations between the second elastification means in the subsequent belly section. The maximum separation between the second elastification means in the subsequent back section is advantageously larger than the maximum separation between the second elastification means in the subsequent belly section.

The second elastification means advantageously also have a fanning-out degree of $$F=(A-B)/B*100\%$$

of 50 to 900%, in particular 100 to 700%, and moreover, in particular 150 to 550%.

The fanning-out degree F. is thereby defined as the ratio between the separation increase (A−B) and the minimum separation (B) in percent. The values A and B are thereby defined as the separation between the outermost second elastification means in the longitudinal direction of the subsequent incontinence article and the innermost second elastification means in the longitudinal direction (i.e. not the separation between directly neighboring second elastification means), i.a. A as the maximum separation, in particular, on the subsequent longitudinal edge of the crotch section or on the subsequent absorbent body edge, and B as the minimum separation, in particular, in the subsequent side seam area.

The fanning-out degree F. of the second elastification means is advantageously larger in the subsequent back section than in the subsequent belly section.

It may also be advantageous to deactivate the elastic properties of the second elastification means in an overlapping area with the absorbent body. This deactivation may e.g. be realized by a number of separating cuts through the second elastification means in the overlapping area with the absorbent body. Other separating methods are also feasible, e.g. ultrasound welding or laser welding. The elastic properties of the first elastification means may also be deactivated in the overlapping area with the absorbent body.

The extension of the second elastification means and the performance of the second contour cut of the partial webs are advantageously such that the second contour cut is performed along and at a separation (D) from the innermost second elastification means in the longitudinal direction facing the crotch area. This separation (D) is advantageously 2 to 40 mm, in particular 3 to 30 mm, and moreover in particular 4 to 20 mm.

The first and/or second elastification means 28, 40, 42 are advantageously fixed to the partial webs under a pretension of 1.5 to 6.0, in particular 2.5 to 5.0. The pretension is thereby defined as the factor of the degree of extension compared to the non-extended/relaxed state of the elastification means.

Thread-shaped or band-shaped elastification means, such as rubber or polyetherpolyurethane or polyesterpolyurethane threads, preferably elastic threads such as LYCRA® or SPANDEX® (elastane) threads, are advantageously used as the first and/or second elastification means. The first and/or second elastification means preferably have a thickness of 300 to 1500 dtex, in particular 500 to 900 dtex, moreover in particular 500 to 600 dtex.

The first and/or second elastification means are advantageously fixed to the partial webs by means of glue. The glue for fixing the first and/or second elastification means may thereby advantageously be applied directly onto the partial webs and/or non-woven cover layers or directly onto the elastification means (thread glue application). The first elastification means are preferably directly provided with glue, in particular by spraying, and the second elastification means are disposed on the glue that has been previously extensively applied to the partial webs and/or non-woven material cover layers.

In accordance with a further preferred embodiment of the inventive method, the second contour cut only includes the partial webs and not the crotch section. For this reason, a discontinuous shape may be formed along the leg openings at the transition area between the crotch section and the belly section or back section.

In accordance with a preferred embodiment of the inventive method, the second contour cut of the partial webs is performed in such a fashion that the curved leg cut-out of the partial web of the subsequent belly section extends in a different shape, in particular a different angle or radius than the curved leg cut-outs of the partial web of the subsequent back section.

In accordance with a preferred embodiment, the second contour cut for forming the substantially curved leg cut-outs is performed in such a fashion that the second contour cut is simultaneously realized both for the partial web of the subsequent belly section and the partial web of the subsequent back section.

In a particularly preferred embodiment, the second contour cut is performed using a cutting roller pair, i.e. a rotational knife with an anvil roller.

In another advantageous fashion, the superposed partial webs are joined to form side seam areas of the incontinence article to be produced and the separating cut is performed in the same method step.

BRIEF DESCRIPTION OF THE DRAWING

Further features, details and advantages of the invention can be extracted from the accompanying claims, the drawing and the following description of an incontinence article in the form of pants and of the inventive production method. In the drawing:

DESCRIPTION OF THE PREFERRED EMBODIMENT

Figure 6:
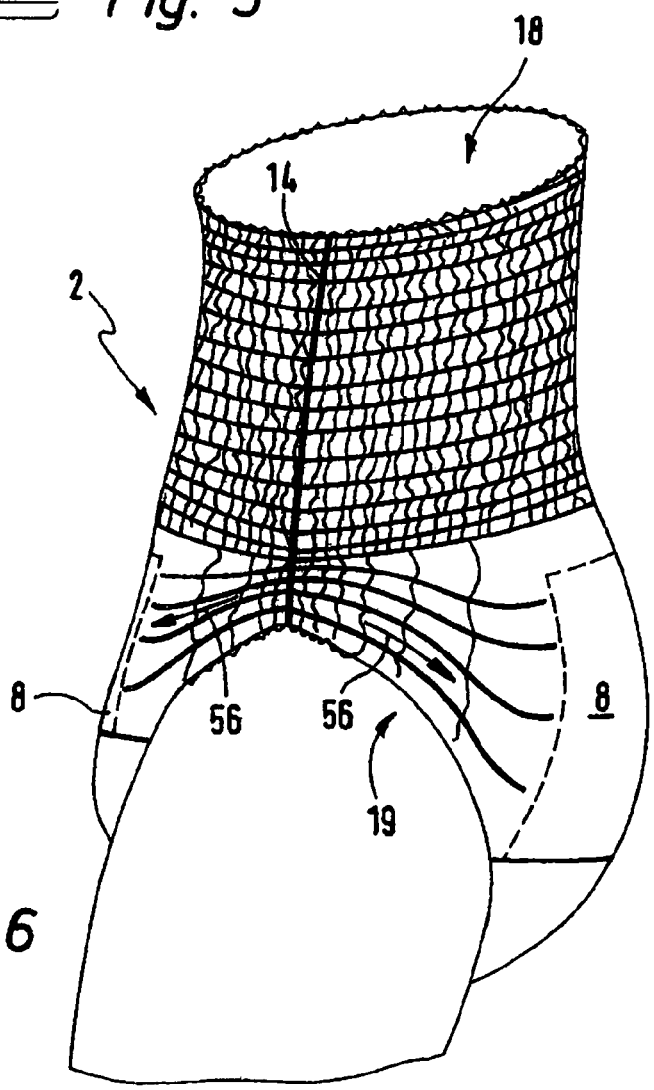
FIG. 6 shows a perspective view (schematic) of the incontinence article according to FIG. 1, which is applied to a user.

The figures show an incontinence article in the form of pants, which is designated in total by reference numeral 2, for receiving solid and liquid body excrements. The incontinence article 2 is formed from three components which can be largely independently produced, i.e. a front belly section 4, a rear back section 6, and a crotch section 8 which is disposed therebetween and comprises an absorbent body 7, wherein the crotch section 8 overlaps a substantial surface portion of the belly section 4 and also of the back section 6, and is permanently connected in the overlapping area during production. As can be gathered from FIG. 1, this yields an H-shaped basic structure of the incontinence article with a longitudinal direction 9. The joined components (FIG. 1) are then also connected to each other at the respective lateral longitudinal edge sections 10, 12 of the belly section 4 and the back section 6 during production in order to form the pants shape (schematically shown in FIG. 6), thereby forming side seam areas 14 on both sides (FIG. 6). In this pants-shaped state of the incontinence article, which is realized by the manufacturer, the belly section 4 and the back section 6 continuously extend in the transverse or peripheral hip direction 16 to the side seam areas 14 and thereby define a hip opening 18, which is closed in the peripheral hip direction, and leg openings 19 through which the user applies the incontinence article like a pair of pants.

The belly section 4 can be divided into an area 20 on the hip side and an area 22 on the crotch side facing the leg openings. A corresponding subdivision is provided in the back section 6, i.e. also into an area 24 on the hip side and an area 26 on the crotch side facing the leg openings.

First elastification means 28 are provided in the area 20 of the belly section 4 on the hip side and in the area 24 of the back section 6 on the hip side, which may be, in particular, thread-like elastification means, such as LYCRA® (elastane) threads, which are pretensioned and connected to the sheet materials (chassis materials) of the belly section 4 and the back section 6 in a so-called stretch-bond method. These first elastification means 28 extend in the transverse or peripheral hip direction 16 from one side seam area 14 to the other.

The section 22 of the belly section 4 or 26 of the back section 6 on the crotch side facing the leg openings 19 has an edge contour 32 or 34 which extends towards a transverse center axis 30 of the crotch section 8 and differs from the transverse or peripheral hip direction 16. This edge contour 32, 34 is also curved in the representation of FIG. 1 and therefore suited to delimit the leg openings 19. The shape of the area 22 or 26 on the crotch side facing the leg openings also realizes a relatively large overlapping area 36, 38 between the crotch section 8 and the belly section 4 or back section 6, which is essential in view of a tear-resistant connection between the crotch section 8 and the belly section 4 or back section 6. The larger the overlapping area 36, 38, the smaller the amount of glue required with respect to the surface, which is advantageous with respect to the rigidity of the chassis materials. The components can be connected, in particular, without having to provide glue on the entire surface.

Figure 1:
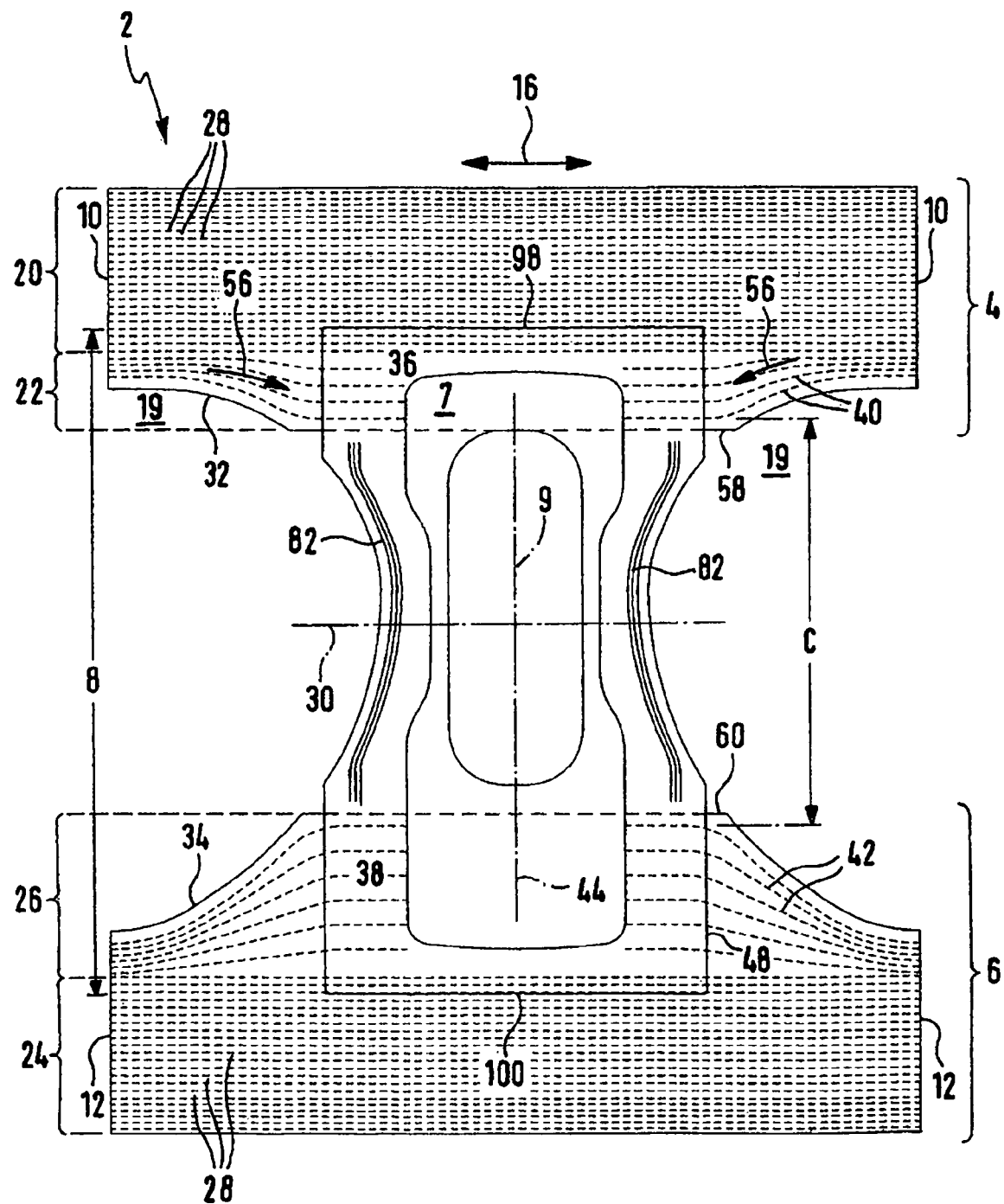
FIG. 1 shows a top view of an incontinence article, which shows a belly section, a back section and a crotch section that connects them, of the incontinence article, which are not yet connected to form a pants shape, but are illustrated in a flat and extended state.
Figure 2:
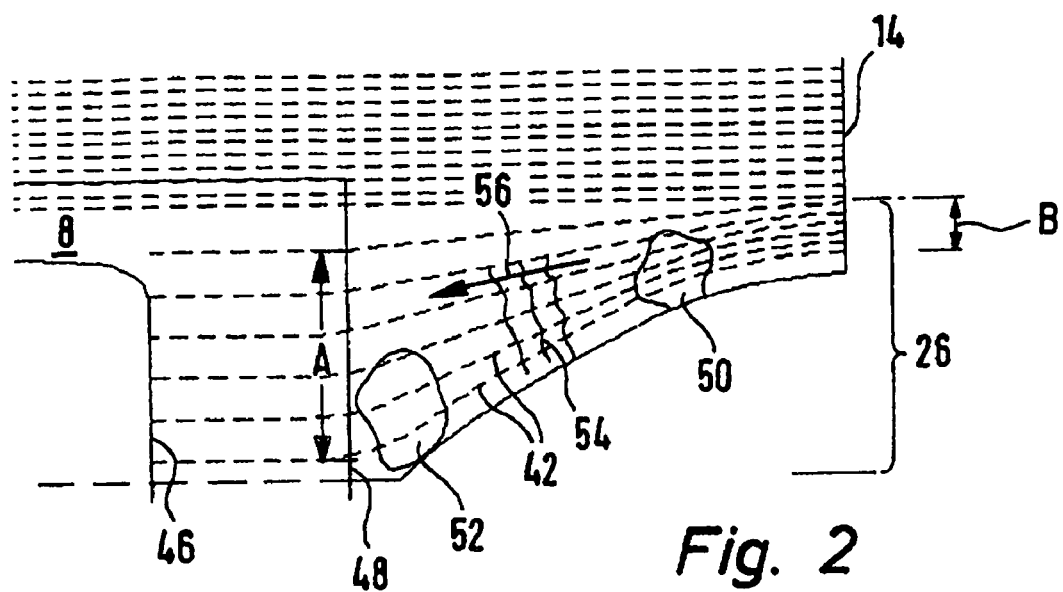
FIG. 2 shows a detail of the incontinence article of FIG. 1.
Figure 3:
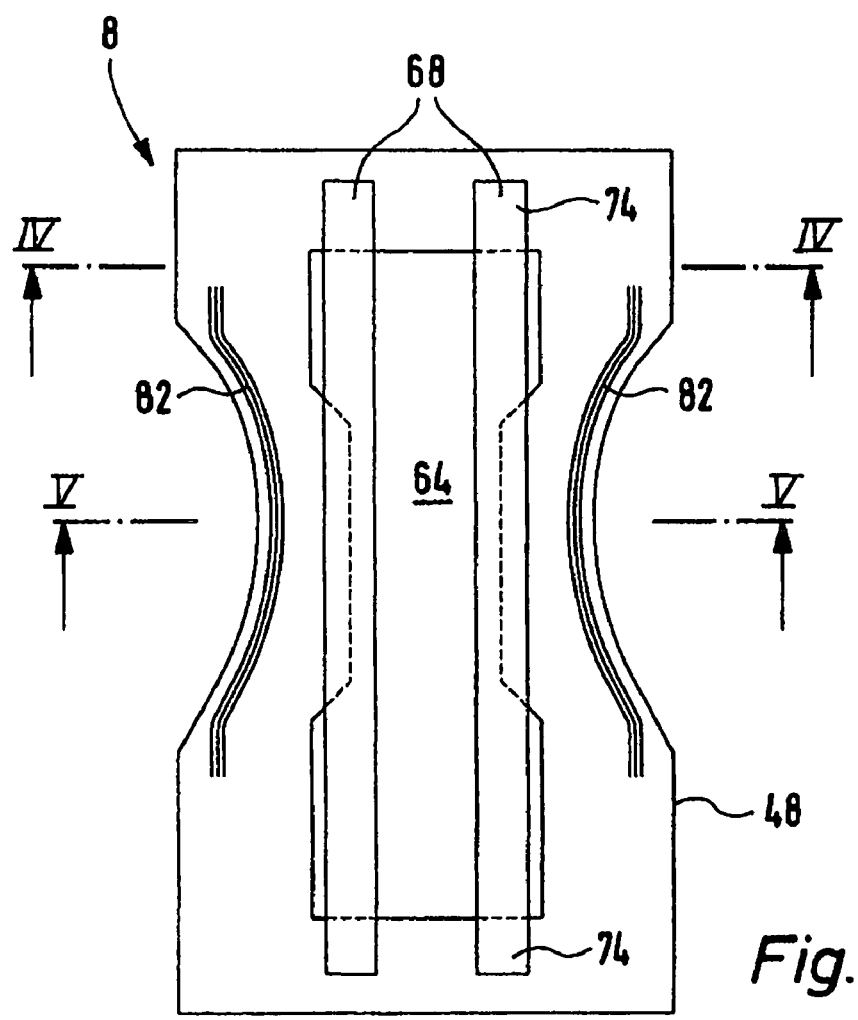
FIG. 3 shows a top view of the crotch section of the incontinence article according to FIG. 1, in turn, in the flat and extended state.

The respective area 22, 26 of the belly section 4 or the back section 6 on the crotch side facing the leg openings 19 is also elasticised. Second elastification means 40 and 42 are provided at that location. The second elastification means 40, 42 extend in each case starting from the side seam areas 14 towards a longitudinal center axis 44 of the incontinence article. As is illustrated in FIGS. 1 and 2, the second elastification means 40, 42 fan out towards the longitudinal center axis 44. This means that the separation between them increases towards the longitudinal center axis 44. This fanning out of the second elastification means 40 and 42 can also be quantitatively described in more detail with respect to FIG. 2. The second elastification means 42 (shown in FIG. 2) of the back section 6 e.g. have a minimum separation of 3 to 8 mm from each other in the side seam areas 14 (separation of directly neighboring elastification means) and a maximum separation (separation of directly neighboring elastification means) of 7 to 35 mm on an absorbent body edge 46 or longitudinal edge 48 of the crotch section 8. The fanning-out degree F. can also be defined with respect to FIG. 2:

$$F = (A-B)/B * 100\%$$

This fanning-out degree may advantageously be between 50 and 900%, in particular between 100 and 700%, and moreover, in particular between 150 and 550%. It is advantageously larger in the back section 6 than in the belly section 4. The values A and B are thereby defined as the separation between the outermost second elastification means 40, 42 in the longitudinal direction 9 and the innermost second elastification means 40, 42 in the longitudinal direction 9, (i.e. not the separation between directly neighboring elastification means), i.e. A as the maximum separation, in particular, on the longitudinal edge 48 of the crotch section 8 and B as the minimum separation, in particular, in the side seam area 14.

When the fanning-out degree of the second elastification means 40, 42 is selected sufficiently large, the restoring force can thereby be reduced within the area 22 or 26 on the crotch side facing the leg openings 19 in the direction 56 towards the crotch section 8 by ensuring that the pretension is not excessively increased due to the larger path of the second elastification means 40, 42 in consequence of the curved extension of the second elastification means 40, 42 facing away from the hip or transverse direction 16. A comparison of a region 50, which is disposed closer to the side seam area 14 of the relevant crotch-side area 22 or 26, with a region 52, which is disposed closer to the crotch section 8, shows that the restoring force that is generated when the region 52 is extensively stretched (extension in the direction of the elastification means 42) is smaller than the restoring force that is produced when the region 50 is stretched. In consequence of the smaller elastic forces that are exerted by the second elastification means 40, 42 in the illustrated exemplary case, the chassis materials of the belly section 4 and back section 6 are advantageously less gathered, such that the number of folds/crimps 54 is also reduced, starting from the respective side seam area 14 in the direction 56 towards the crotch section 8. Since the restoring forces that are generated through extensive stretching of the belly section in the area 22 of the belly section 4 or area 26 of the back section 6 on the crotch side facing the leg openings decrease in the direction of the arrow 56, i.e. in general from the side seam area 14 towards the crotch section 8, the wear comfort is considerably improved, since, as was established in accordance with the invention, the use of elastically stretchable materials is particularly problematic especially in these areas, since these materials are particularly strained with respect to tension and extension at these locations in correspondence with the physiology of the body shape of a person. The deliberate inventive reduction of this restoring force, i.e. decreasing restoring force in the direction of arrow 56, i.e. in the direction approaching the crotch section 8, provides a degree of freedom which could not be achieved before, and solves the above-mentioned problems.

Figure 8:
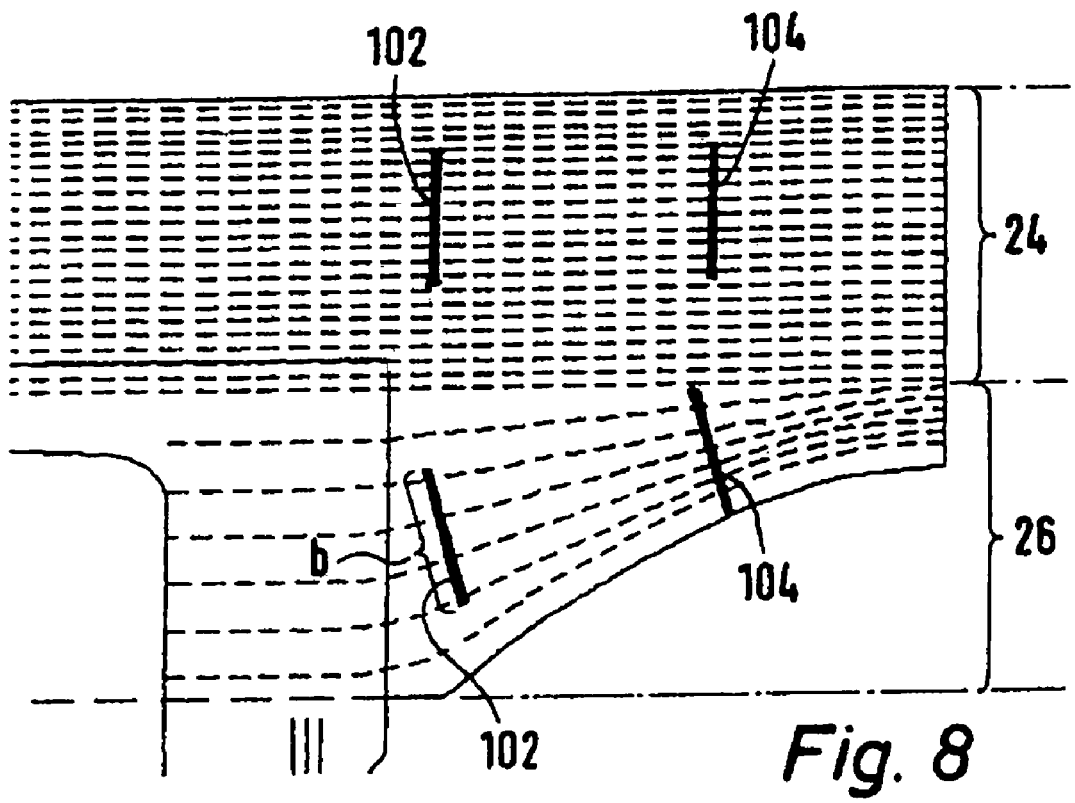
FIGS. 8, 9 clearly show as an example the determination of restoring forces in the belly section or back section of the incontinence article.
Figure 9:
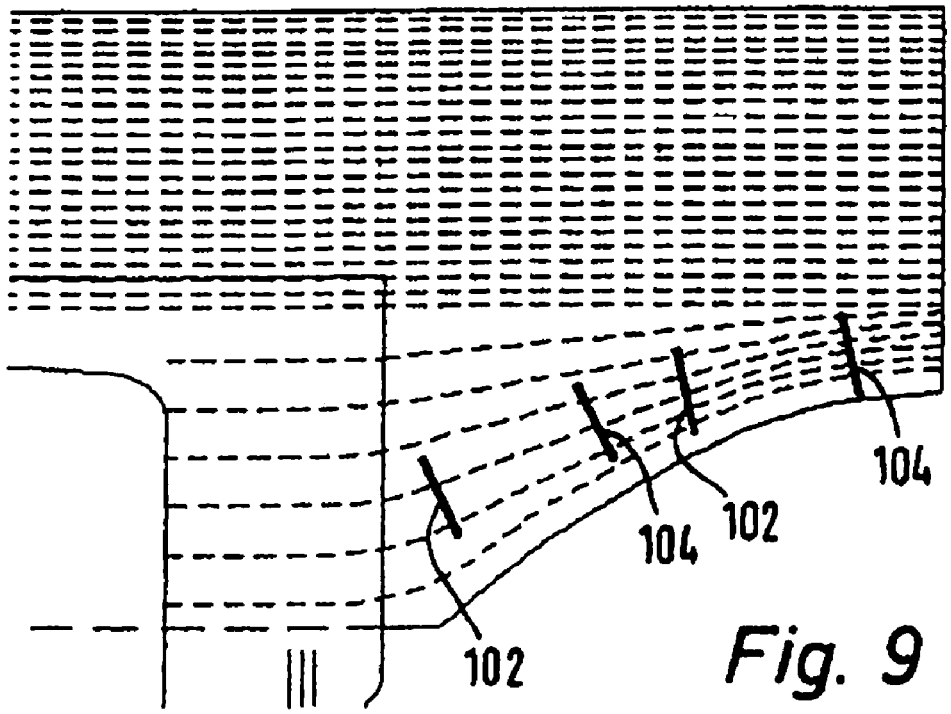

As mentioned above, restoring forces can be determined directly on the chassis of the incontinence article. Towards this end, the relevant area of the belly section 4 or of the back section 6 is clamped between two clamping jaws 102, 104 (FIG. 8) of defined identical clamping jaw width (b), and the restoring forces are then determined under defined extension of the areas to be measured of, in particular, 30% or 50% or 80% of the initial length (of the clamping jaw separation in the unclamped state) to simulate the extension exerted during use. The clamping jaws 102, 104 are thereby moved apart from each other. The clamping jaws 102, 104 should fix a maximum amount of, however at least two, neighboring elastification means 40, 42 or 28 of the area to be measured and should be substantially oriented at right angles with respect to the extension of the elastification means, such that the clamping jaws 102, 104 are extended, i.e. moved apart from each other, substantially in the direction of extension of the elastification means. This is clearly shown in FIGS. 8 and 9. FIG. 8 shows, in principle, the arrangement of clamping jaws 102, 104 in order to compare the restoring forces in the area 22, 26 on the crotch side facing the leg openings with the restoring forces in an area 20, 24 on the hip side. FIG. 9 shows, in principle, the arrangement of clamping jaws 102, 104 in order to compare the restoring forces in a region closer to the crotch section 8 with the restoring forces in a region closer to the side seam area 14.

In the illustrated preferred embodiment of the incontinence article 2, a separation C between the innermost second elastification means 40 of the belly section 4, facing the crotch area, and the corresponding innermost second elastification means 42 of the back section 6, facing the crotch area, is between 250 and 420 mm depending on the size of the incontinence article. The second elastification means 40, 42 substantially extend to the transverse edge 58, 60, facing the crotch area, of the belly section 4 and the back section 6. The separation between the belly section 4 and the back section 6 in the longitudinal direction 9 is 250-400 mm.

The separation between the innermost second elastification means 40, 42, facing the crotch area, and the edge contour 32, 34, defining the leg openings, of the area 22, 26 of the belly section 4 and the back section 6 on the crotch side facing the leg openings is preferably 2 to 40 mm, moreover, in particular, preferably 3 to 30 mm, in particular preferably 4 to 15 mm.

The belly section 4 and the back section 6 extend in the side seam area 14 in the longitudinal direction 9 preferably by between 100 and 220 mm. The maximum extension of the crotch section 8 in the transverse direction 16 is advantageously 200 to 350 mm.

Figure 4:
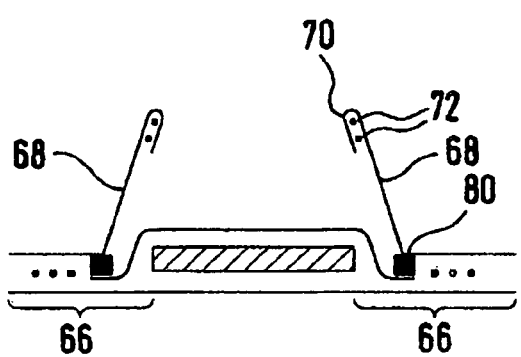
FIG. 4 shows a cross-section (schematic) along a transverse center axis of the crotch section with intersecting plane IV-IV in FIG. 3.
Figure 5:
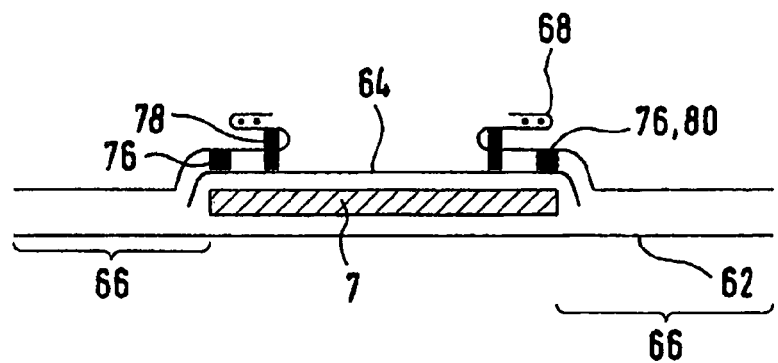
FIG. 5 shows a cross-section corresponding to FIG. 4 (schematic) of the crotch section with intersecting plane V-V of FIG. 3, with unfolded and upright barrier means.

The crotch section 8 comprises a liquid-impermeable backsheet material 62, which may be formed, in particular, by a breathable, but liquid-tight foil material, and a topsheet material 64 that is preferably based on a non-woven material. The absorbent body 7 is disposed between the backsheet material and the topsheet material (shown in FIGS. 4, 5). In the exemplary case, the backsheet material 62 forms a projection 66 that extends past the absorbent body 7 in the transverse direction 16. The topsheet 64 only slightly projects past the absorbent body 7 in the transverse direction. However, one upright barrier means 68 is provided on each side of the absorbent body 7, which extends in the longitudinal direction 9 and is typically called an upright cuff element or collar element, and is preferably formed from a hydrophobic, in particular, liquid-impermeable non-woven material, which preferably extends in the transverse direction 16 to the lateral longitudinal edges 48 of the crotch section 8. The distal ends 70 of the barrier means 68 are provided with further elastification means 72, which lift the barrier means 68 against the skin surface of the user during use of the incontinence article, as is schematically shown in FIG. 5. In their respective longitudinal end areas 74, the lateral barrier means 68 are fixed via schematically indicated fixations 76, 78 to the topsheet 64 or to themselves in a C-shaped folded configuration. It is thereby advantageous and notable that each inner fixation 78 in FIG. 4 fixes the barrier means 68 onto itself in the transverse direction 16 within the outer fixation 76, which forms a cuff base line 80 that continuously extends in the longitudinal direction 9. However, the inner fixation 78 is only provided in the longitudinal end areas 74 of the barrier means 68.

It is thereby particularly advantageous for the above-mentioned projection 66 of the backsheet material 62 and/or the topsheet material 64 which extends past the absorbent body 7 on both sides of the absorbent body, i.e. on the left-hand and right-hand side added together, to be at least 25% with respect to the largest width of the crotch section 8. This provides space in the transverse direction 16 for the arrangement of leg elastification means 82 that extend along the leg openings 19. It has turned out to be advantageous for the leg elastification means 82 to extend at a given separation from the absorbent body 7 which comprises a great deal of material and is therefore rather rigid in order not to exert any additional extension or torsional forces onto the absorbent body, which could impair its absorption properties, and also to realize a liquid-tight leg termination which is largely independent of the absorbent body. In the present case, it has turned out to be particularly advantageous for the leg elastification means 82 to terminate in the longitudinal direction 9 at a clear distance of, in particular, at least 10 mm, preferably at least 20 mm, upstream of the second elastification means 40 and 42 of the belly section 4 or the back section 6. These leg elastification means 82 preferably terminate in the longitudinal direction 9 upstream of the belly section 4 and the back section 6. This is advantageous and essential since, in this case, the leg elastification means 82 do not or hardly influence the stress behavior of the belly section 4 and the back section 6. It was found out that, in view of the inventive aim of improving the wear comfort, in particular, in the areas 22 and 26 of the belly section 4 and back section 6 on the crotch side facing the leg openings 19, it is disadvantageous for the leg elastification means 82, which usually have a great pretension and correspondingly large restoring forces, to additionally also extend at that location.

As is illustrated in FIG. 1, the crotch section 8 projects to a relatively large extent 66 past the absorbent body 7 in the transverse direction, in particular, also in areas of the crotch section 8, which face the belly section 4 or the back section 6. As mentioned above, this yields a relatively large overlapping area 36, 38 between the crotch section 8 and the belly section 4 and the back section 6. According to a preferred embodiment variant, the overlapping area 36 of the crotch section 8 and belly section 4 covers at least 12% of the surface of the belly section 4, and the overlapping area 38 of the crotch section 8 and the back section 6 covers at least 20% of the surface of the back section 6. This is advantageous, since the crotch section 8 is thereby reliably fixed to the belly section 4 or the back section 6 even when the glue is not provided on the full surface. It is thereby also advantageously sufficient to use glue only in sections or in a pattern in order to realize a connection. This advantageously prevents the joined materials from becoming excessively rigid.

Figure 7:
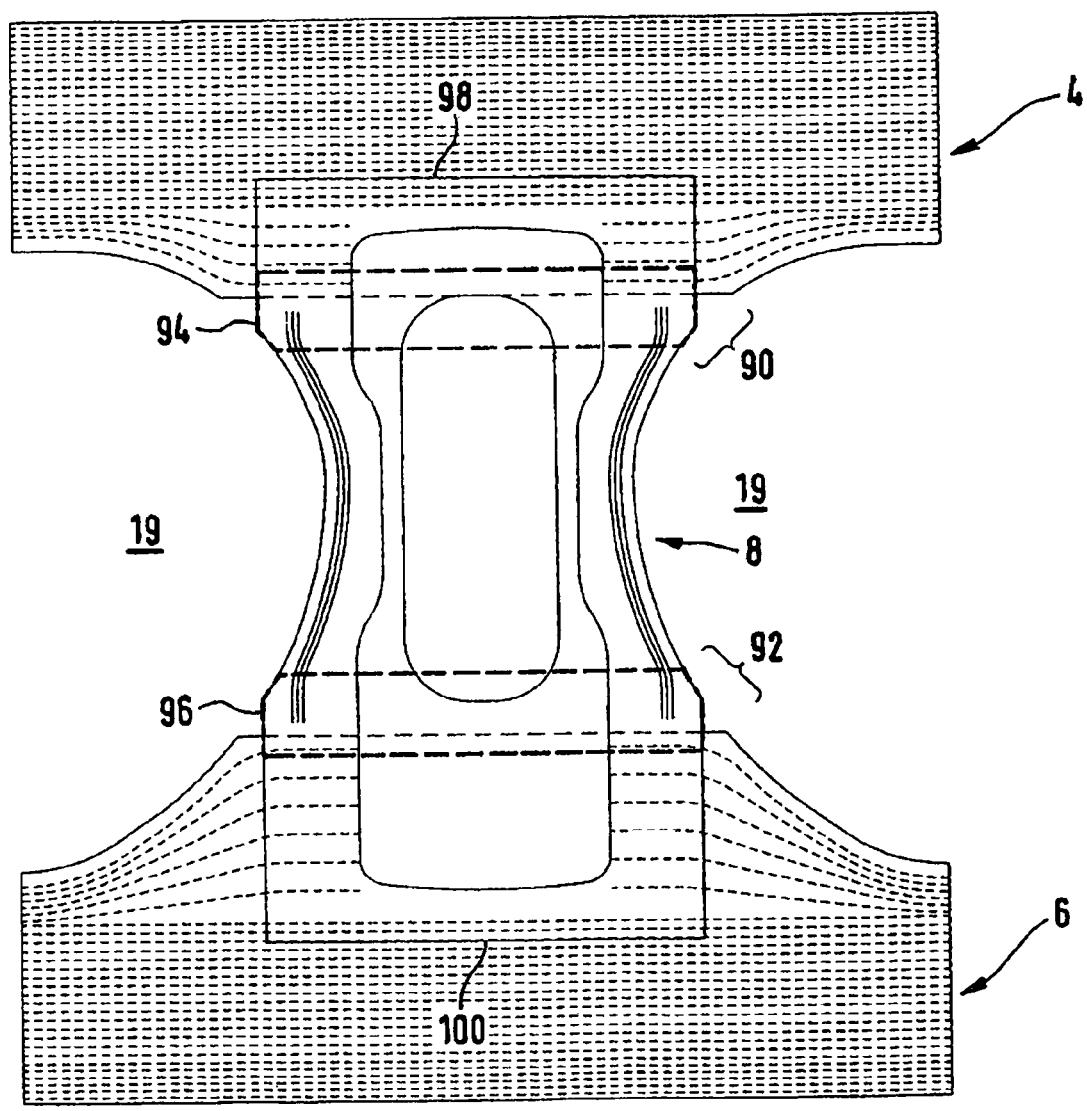
FIG. 7 shows a top view of the incontinence article corresponding to FIG. 1 to clearly show the connection between the crotch section and the belly section or back section.

Another advantageous detail of the inventive incontinence article is explained with respect to FIG. 7, which corresponds to FIG. 1. The three-component concept for producing the inventive incontinence article produces a transition 90 between the crotch section 8 and the belly section 4, as well as a transition 92 between the crotch section 8 and the back section 6, which usually yields a non-continuous shape, i.e. with corners or angles or bends, of the edges of the chassis materials, which define the leg openings 19. This is dangerous in that force peaks are formed in the area of the transitions 90, 92, which could tear the chassis materials, which could, in turn, impair joining of the crotch section 8 to the belly section 4 or the back section 6. To counteract this, the liquid-impermeable backsheet material 62 of the crotch section 8 is provided with a reinforcing coating 94, 96 in the respective transition 90 and 92. It is sufficient to provide this reinforcing coating 94, 96 only in the area indicated by the dashed line of FIG. 7. In the exemplary, advantageously illustrated case, the reinforcing coating 94, 96 overlaps the belly section 4 and the back section 6 in the longitudinal direction 9 by only approximately 10 to 20 mm, in particular, by approximately 15 mm.

The reinforcing coating terminates in the longitudinal direction 9 in each case upstream of the longitudinal ends 98, 100 of the crotch section, at least 30 mm upstream of the belly-side longitudinal end 98 and at least 90 mm upstream of the back-side longitudinal end 100. This is advantageous in that the reinforcing coating 94, 96 does not thereby unnecessarily reinforce the chassis materials in areas where this is not helpful but rather undesired and disadvantageous. This also saves material costs. However, the possibility to provide the reinforcing coating 94, 96 not only in the transition 90 or 92 remains unaffected.

The reinforcing coating 94, 96 advantageously consists of a spunbonded non-woven material of polypropylene having a surface density of 10 to 20 g/m$^2$, in particular 12 to 17 g/m$^2$.

Figure 10:
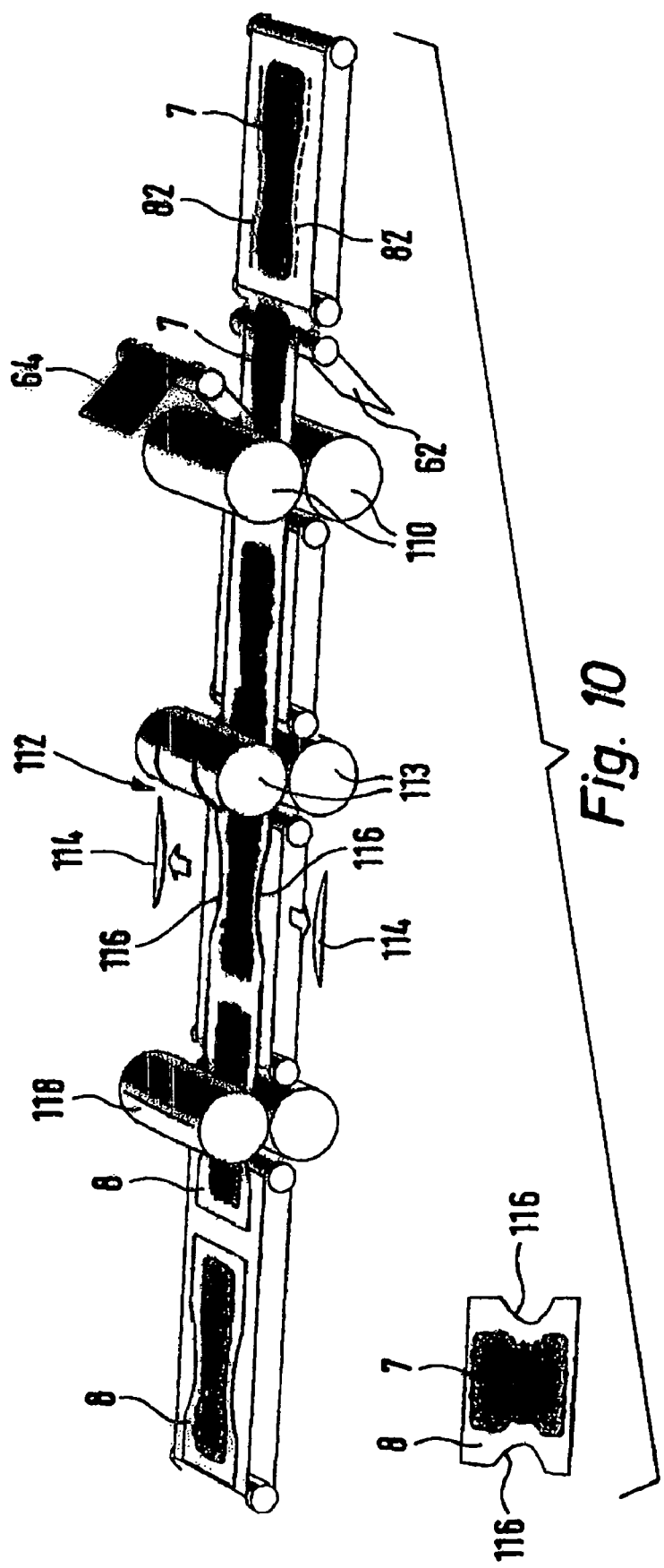
FIG. 10 schematically shows the inventive method for producing the crotch section.

Inventive Method:

FIGS. 10 through 13 show the inventive production method. FIG. 10 shows the production of crotch sections 8. Towards this end, an endless backsheet material web 62 and an endless topsheet material web 64, and, in succession, the absorbent body 7 and (only indicated) the leg elastification means 82 that are associated with the subsequent leg openings, are supplied to a fast running production machine. The absorbent bodies 7 are disposed at a separation from each other between the topsheet material web 64 and the backsheet material web 62 and the composite that is thereby formed is fixed through suitable joining means, in particular glue. The leg elastification means 82 are also supplied and fixed between the topsheet material web 64 and the backsheet material web 62. This is realized by a first roller pair 110 and a glue in a fashion that is not illustrated. For completeness, it should be mentioned that the crotch section 8 additionally comprises lateral upright and preferably elasticised cuffs as side leakage protection. In the present case, these are already provided on the side of the topsheet material web 64 facing the body but are not shown. They may also be introduced at any point of the production process (FIG. 10) or at a later point.

Continuing in the supply direction, the composite is subjected to a first contour cut 112 using a cutting roller pair 113. During the contour cut 112, curved segments 114 are cut out of the crotch-section 8-forming composite of backsheet material web 62 and topsheet material web 64 to thereby form leg cut-outs 116 for the crotch section 8. The composite is then supplied to a downstream cutting station 118 where a separating cut is performed transversely to the supply direction for singling the crotch sections 8 of the incontinence article to be produced. FIG. 10 also indicates a perspective view of the crotch section 8 with absorbent body 7 and leg cut-outs 116.

Figure 11:
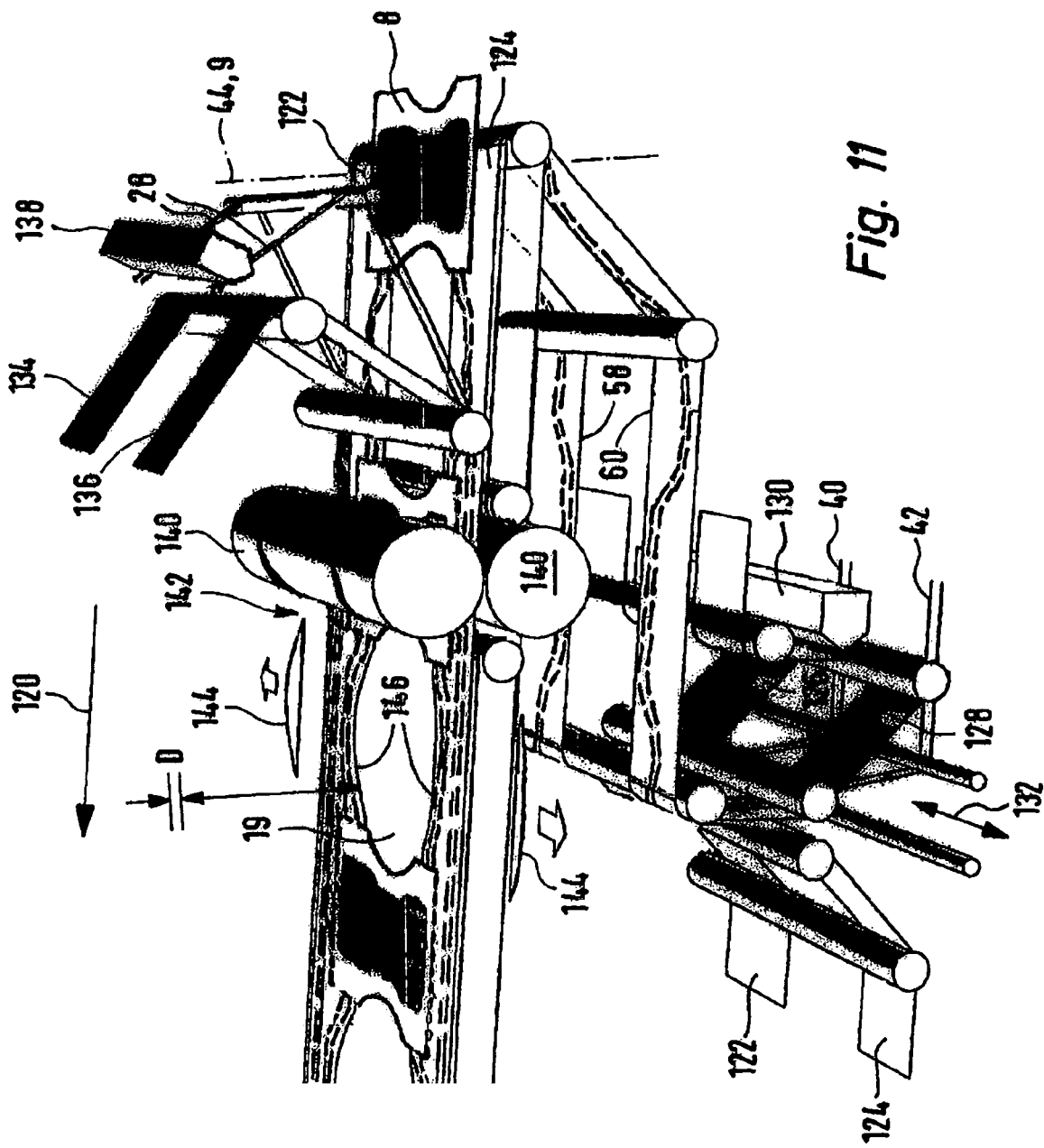
FIG. 11 schematically shows how the partial sections are supplied and joined to the crotch section and the performance of a second contour cut.
Figure 12:
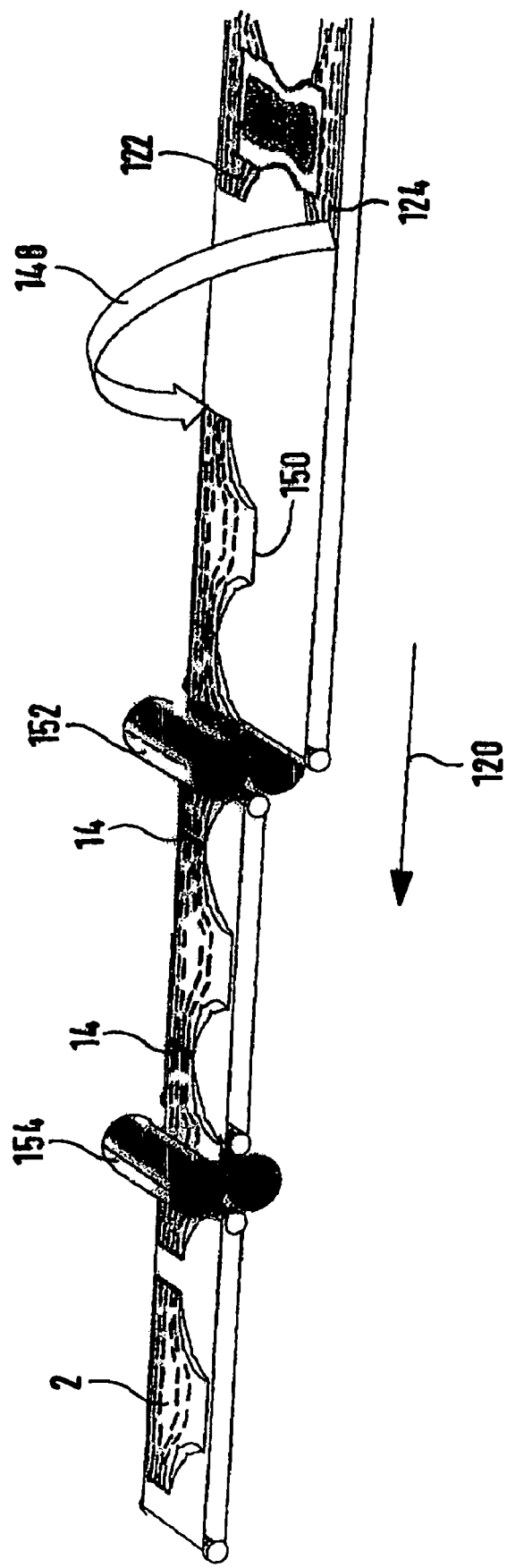
FIG. 12 schematically shows how the pants shape is folded, the side seam areas are formed and the hygiene articles are subsequently separated.

After separating the crotch sections 8, the crotch sections are turned through 90° during continued supply, and are then further supplied in a direction transverse to the subsequent longitudinal center axis 44 of the incontinence article 2 in the machine direction 120 (FIG. 11). As is also shown in FIG. 11, partial webs 122, 124 on the basis of non-woven material are supplied for producing the subsequent belly section 4 and back section 6 of the incontinence article. These partial webs 122, 124 may be formed starting from one single web through separation in the longitudinal direction. The above-mentioned second elastification means 40 and 42 are disposed onto these partial webs 122, 124, and are thereby also supplied in an endless fashion and in the supply direction of the partial webs 122, 124. For fixing the second elastification means 40, 42 to the partial webs 122, 124, one non-woven cover layer 126, 128, which was previously loaded with glue in a glue application station 130, is applied such that the second elastification means 40, 42 are laminated between the partial webs 122, 124 and the non-woven cover layers 126, 128. FIG. 11 is a schematic view and therefore does not explicitly show that the second elastification means 40, 42 are supplied at a varying separation from each other, which is realized by an oscillating guiding means (indicated by the double arrow 132). The curved fanning-out shape of the second elastification means 40, 42 in the direction towards the crotch section 8 is thereby formed through corresponding control of the guiding means for each individual elastification means 40, 42.

The partial webs 122, 124 are then further supplied in the above-mentioned composite and joined with the crotch sections 8 such that one end of the crotch sections overlaps the partial web 122 in a longitudinal direction 9 transversely to the machine direction 120 and the other end thereof overlaps the other partial web 124. The crotch sections 8 are supplied in such a fashion that, after being joined, they are disposed at a separation from each other in the machine direction. The crotch sections 8 and the partial webs 122, 124 are fixed to each other in the configuration obtained from FIG. 11, and are further transported in the machine direction 120.

The first elastification means 28 that extend in the transverse or peripheral hip direction 16 are then supplied in an endless fashion in the machine direction 120 and fixed to the partial webs 122, 124. Non-woven material webs 134, 136 are again supplied. However, the glue is not directly applied onto the non-woven material webs 134, 136 but is disposed onto the first elastification means 28. The first elastification means 28 are then disposed on the partial webs 122, 124 and covered by the non-woven material webs 134, 136 such that they are laminated.

It is also feasible to provide each individual elastification means 28, 40, 42 with glue, i.e. to glue each thread. It is also feasible to omit the elastification means 28, 40, 42 and the non-woven cover layers 126, 128, 134 and/or 136 irrespective of the way in which the glue is applied. However, the non-woven cover layers are advantageous in that they simultaneously form a soft inner side of the incontinence article.

Subsequent thereto, FIG. 11 shows a further cutting roller pair 140, i.e. a rotating knife with an anvil roller, between which the previously formed composite is guided through in the machine direction 120 with the described orientation. A second contour cut 142 is thereby performed, in the course of which one respective curved segment 144 is advantageously separated from each partial web 122, 124, i.e. from the mutually facing transverse edges or edge sections 58 and 60 of the partial webs 122, 124, to also form leg cut-outs 146 for the partial webs 122, 124. Since the second contour cut 142 does not include the crotch section 8 but only the partial webs 122, 124 the second contour cut 142 extends substantially along the machine direction 120 in any case at a small angle transversely thereto. In this fashion, the cut can be optimally configured like the first contour cut 112 during production of the crotch section 8. On the whole, the subsequent leg openings 19 of the incontinence article 2 can be formed with high precision in accordance with the optimum requirements. The second contour cut 142 may thereby advantageously have a different shape on the partial web 122 than on the partial web 124. The shape of the leg cut-outs 146 and the subsequent leg openings 19 of the incontinence article 2 may thereby have different configurations in the belly section 4 and in the back section 6.

The composite formed in this fashion is further transported and folded onto itself in a folding station 148 (only indicated in FIG. 12) about a folding line 150 that extends in the machine direction 120, such that one partial web 124 comes to rest on top of the other partial web 122. Subsequent thereto, a respective side seam area 14 is formed between the partial webs 122, 124 in a joining station 152, i.e. the actual pant shape is formed. Subsequent to this method step, a separating cut is performed transversely to the machine direction 120 in a separating station 154, which singles the finished incontinence articles 2. It is also feasible to design the joining station 152 at the same time as a separating station, e.g. in the form of a separating welding means, such that the side seam areas 14 are formed and the incontinence articles 2 are singled at the same time.

Figure 13:
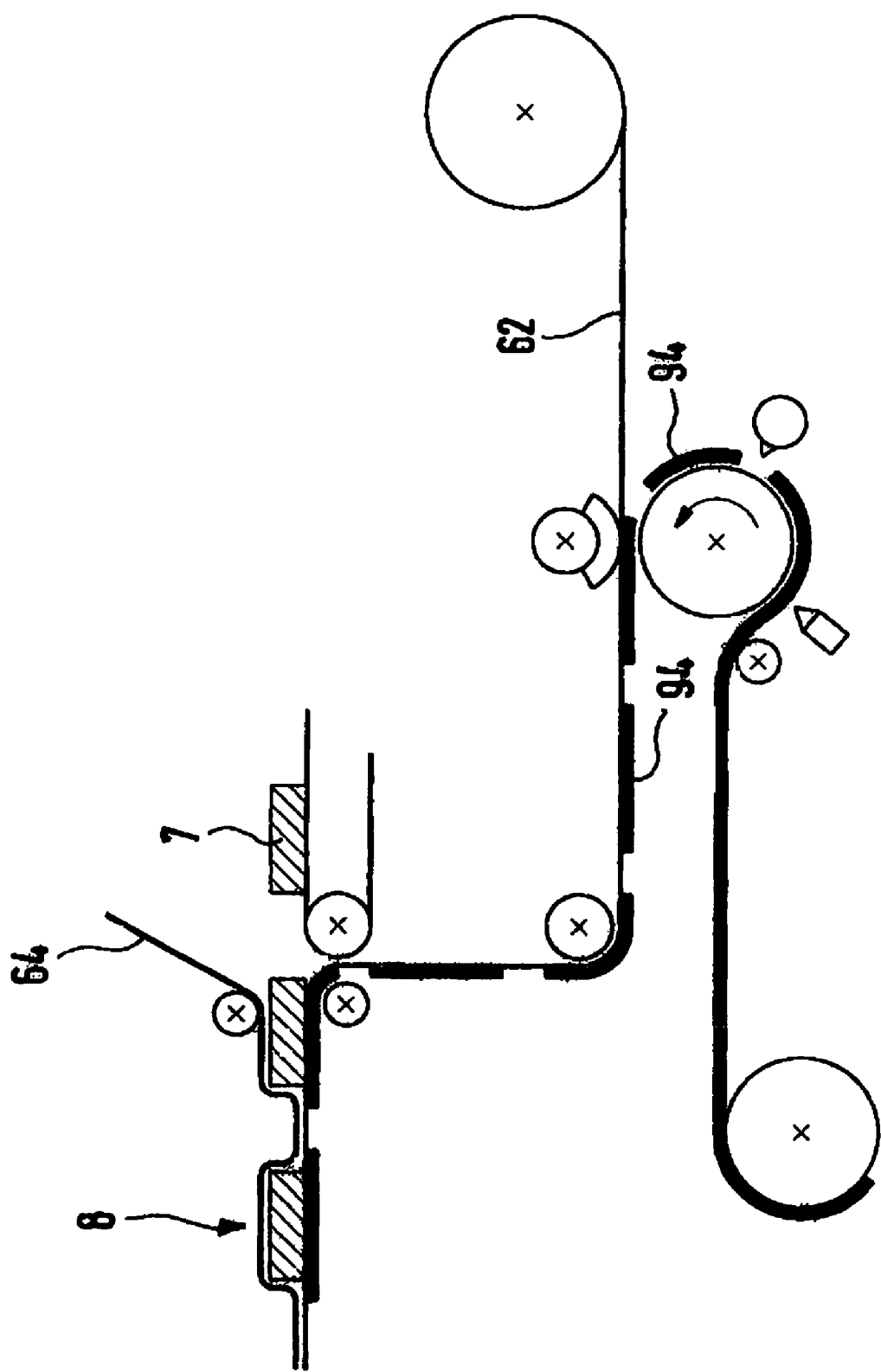
FIG. 13 schematically shows how areas of a backsheet material are coated during the production of the crotch section of the hygiene article.

FIG. 13 finally schematically shows the procedure, wherein sections of the backsheet material web 62 are provided with a reinforcing coating 94 described in connection with FIG. 7, i.e. during supply of the backsheet material web 62 for producing the crotch sections, which was already explained in connection with FIG. 10. In contrast to FIG. 8, the reinforcing coating 94, which may, in particular, be a non-woven material section, extends substantially over a major part of the crotch section 8. The backsheet material web 62 at the longitudinal ends of the crotch section 8 to be formed remains uncoated.

The invention claimed is:

1. A continuous method for producing incontinence articles in the form of pants for receiving body excrements, the articles having a front belly section and a rear back section, which are connected to each other at side seam areas on both sides during manufacture to form a belly and back band that is continuous in a transverse hip direction to define a hip opening that is closed in the peripheral hip direction, the article also having a crotch section with an absorbent body, the crotch section extending in a longitudinal direction between the belly section and the back section, the crotch section being permanently attached to the belly section and the back section, wherein the crotch section, the belly section and the back section define leg openings, the article also having first elastification means disposed in the belly section and in the back section, the first elastification means extending at a separation from and parallel to each other in the transverse hip direction to thereby extensively elasticise the belly section and the back section, and with second elastification means disposed in an area of the belly section and the back section on a crotch side facing the leg openings, the second elastification means starting from the two side seam areas in a direction towards a longitudinal center axis of the incontinence article in a curved shape, thereby fanning out with increasing separation from each other, the method comprising the steps of:

a) supplying crotch sections having absorbent bodies;
a1) performing a first contour cut in the crotch sections, the first contour cut curving inwardly on opposite sides of the crotch section to impart an hour-glass shape to each crotch section;
b) supplying two partial webs having non-woven material, the two partial webs subsequently forming the belly section and the back section of the incontinence article, the two partial webs having a mutual transverse separation from each other and without interposition of an intermediate web;
c) supplying and applying the second elastification means to both partial webs and fixing them thereto such that the second elastification means are disposed, structured and dimensioned to extend from the two side seam areas, subsequently formed in step j), in a direction towards the longitudinal center axis of the subsequently completed incontinence article in a curved shape, thereby fanning out with increasing separation from each other towards the longitudinal center axis;

d) joining the crotch sections with the two partial webs in such a fashion that one end of the crotch sections overlaps one partial web in a longitudinal direction transversely to a machine direction, and an other end thereof overlaps the other partial web, wherein the crotch sections are disposed at a separation from each other in the machine direction;

e) fixing the crotch sections and partial webs in the overlapping areas;

f) forwarding, following steps d) and e), the crotch sections and partial webs in the machine direction;

g) supplying, applying and fixing the first elastification means to the partial webs in the machine direction;

h) performing a curved second contour cut that includes the partial webs on mutually facing edge sections thereof, the first and the second contour cuts thereby defining two leg openings for each incontinence article;

i) folding about a folding line that extends in the machine direction in such a fashion that one partial web comes to rest on top of the other partial web;

j) joining, following step i), the partial webs transversely to the machine direction at a separation from each other for forming side seam areas of the incontinence articles, thereby obtaining products having a belly section, a back section, and an intermediate crotch section; and k) performing a separating cut in a direction transversely to the machine direction to obtain separated, finished incontinence articles.

2. The method of claim 1, wherein following step c), a non-woven cover layer which extends over the second elastification means is supplied to and disposed on each partial web and the two partial webs are further transported in the machine direction at a separation from and parallel to each other.

3. The method of claim 1, wherein following step g), a non-woven cover layer which extends over the first elastification means, is supplied to and disposed on each partial web and the two partial webs are further transported in the machine direction at a separation from and parallel to each other.

4. The method of claim 1, further comprising forming the crotch sections by supplying an endless topsheet material web, an endless backsheet material web and absorbent bodies in a machine direction, the absorbent bodies being disposed at a separation from each other between the topsheet material web and the backsheet material web, securing a composite formed in this fashion and exercising the first contour cut in the composite to form the leg cut-outs of the crotch sections.

5. The method of claim 1, further comprising supplying leg elastification means to the crotch sections.

6. The method of claim 5, wherein the leg elastification means are supplied between a topsheet material web and a backsheet material web.

7. The method of claim 5, wherein the leg elastification means are supplied in such a fashion that they extend at a varying separation from the absorbent body and have a larger separation from the absorbent body at their longitudinal ends than in a center.

8. The method of claim 4, wherein the backsheet material web is supplied in the form of a liquid-ipermeable foil web that is provided with a non-woven coating and/or a reinforcing coating.

9. The method of claim 1, wherein an endless non-woven material web is initially supplied, which is then separated along the machine direction to form the two partial webs.

10. The method of claim 1, wherein the first elastification means which extend in the peripheral hip direction are introduced at a separation from each other of 4 to 10 mm, 4 to 8 mm or 4 to 6 mm.

11. The method of claim 1, wherein the second elastification means are introduced at a varying distance from each other of between 3 mm and 35 mm.

12. The method of claim 1, wherein first and/or second elastification means are fixed to the partial webs under a pretension of 1.5 to 6.0 or 2.5 to 5.0, wherein the pretension is defined as a factor of a degree of extension compared to a non-extended or relaxed state of the first and/or second elastification means.

13. The method of claim 1, wherein the second elastification means are deactivated in an overlapping area with the absorbent body.

14. The method of claim 1, wherein the second contour cut is performed along and at a separation from a respective innermost second elastification means in the longitudinal direction facing the crotch area.

15. The method of claim 14, wherein the separation is 2 to 40 mm, 3 to 30 mm or 4 to 20 mm.

16. The method of claim 1, wherein the second contour cut only includes the partial webs and not the crotch section.

17. The method of claim 1, wherein a curved leg cut-out of the partial web of the subsequent belly section extends in a different shape or at a different angle or radius, than a curved leg cut-out of the partial web of the subsequent back section.

18. The method of claim 1, wherein a transition between the crotch section and the belly section and/or the back section is discontinuous along the leg openings.

19. The method of claim 1, wherein steps j) and k) are performed in a same method step.

* * * * *